United States Patent [19]

Blum

[11] 4,268,268

[45] May 19, 1981

[54] METHOD AND APPARATUS FOR CHARACTERIZATION OF CELLS, PARTICLES, AND LIQUIDS

[76] Inventor: Alvin S. Blum, 2350 Del Mar Pl., Fort Lauderdale, Fla. 33301

[21] Appl. No.: 39,377

[22] Filed: May 16, 1979

Related U.S. Application Data

[63] Continuation-in-part of Ser. No. 972,670, Dec. 26, 1978, and Ser. No. 968,907, Dec. 13, 1978, and Ser. No. 898,998, Apr. 21, 1978.

[51] Int. Cl.³ .................... G01N 33/56; G01N 35/08
[52] U.S. Cl. ........................... 23/230 B; 23/230 R; 23/920; 204/180 G; 422/81; 422/82; 435/291; 435/808
[58] Field of Search ................ 23/230 R, 230 B, 920; 422/81, 82, 72; 356/197, 246; 204/180 G; 435/291, 808

[56] References Cited

U.S. PATENT DOCUMENTS

| | | | |
|---|---|---|---|
| 3,320,148 | 5/1967 | Skeggs | 422/82 X |
| 3,320,149 | 5/1967 | Isreeli | 422/82 X |
| 4,141,687 | 2/1979 | Forrest et al. | 422/67 |

Primary Examiner—Ronald Serwin

[57] ABSTRACT

Method and apparatus for characterizing a population of cells or particles such as blood cells or viruses by automatic means in a flowing stream which comprises: Novel suspending and dispensing means; controlled dispensing of a plurality of portions of the sample population; modification of the suspending milieu, mixing each portion with a different test reagent to elucidate a particular character of the sample; novel electrical separation means; separation of components of said mixture into different streams by said separation means; means for serially measuring properties of at least one of said separated streams to provide a series of measurements relating the reaction of the population to a plurality of different reagents for detailed characterization of said population.

Method and apparatus for characterizing liquids by automatic means in a flowing stream by reaction with specific binding sites on a population of cells or particles employing novel electrical separation means to separate components of the reaction mixture into separate streams, followed by measurement of at least one separated component stream.

24 Claims, 6 Drawing Figures

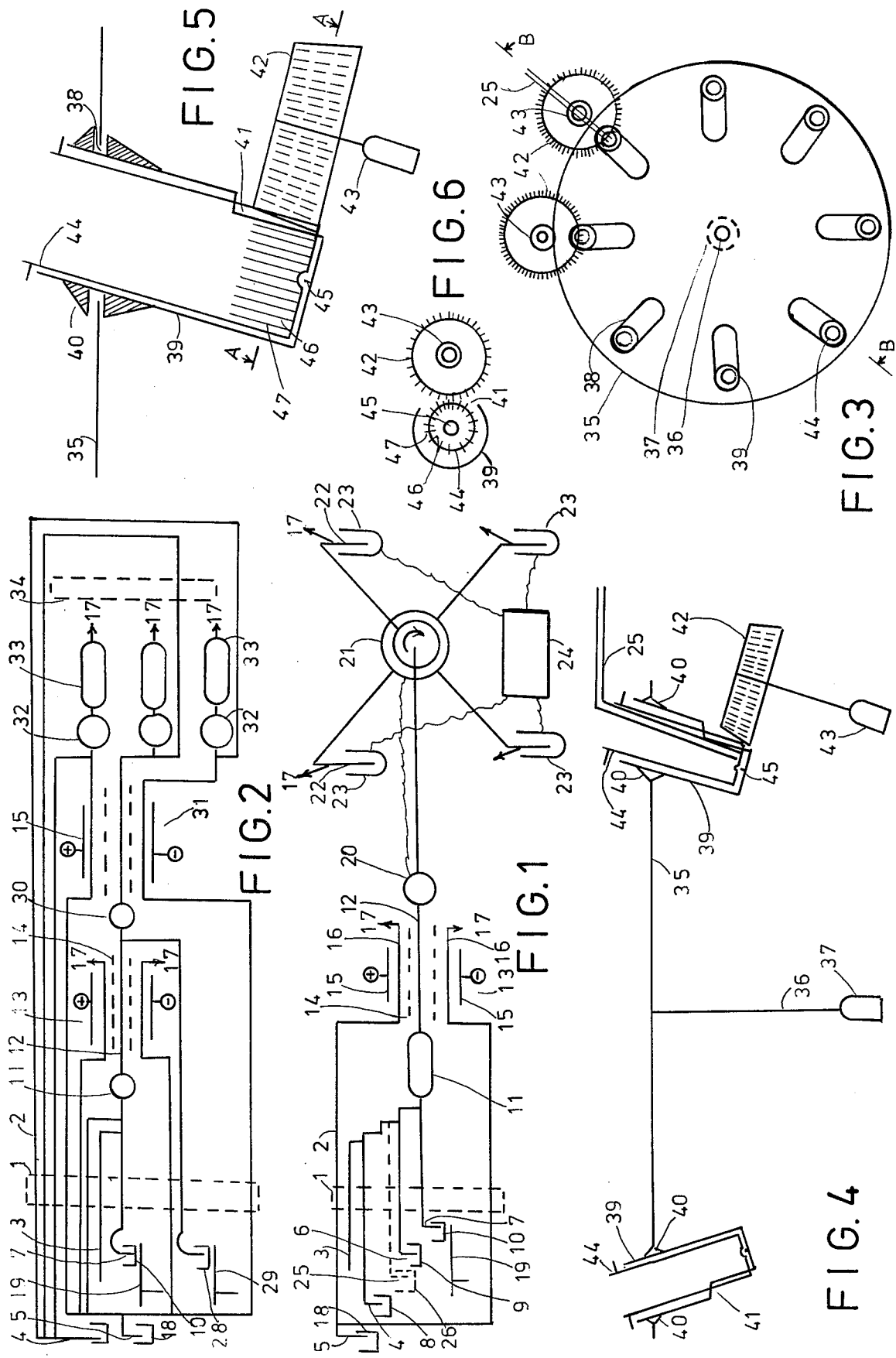

METHOD AND APPARATUS FOR CHARACTERIZATION OF CELLS, PARTICLES, AND LIQUIDS

This is a continuation in part of applications Ser. No. 898,998 filed Apr. 21, 1978, Ser. No. 968,907 filed Dec. 13, 1978, Ser. No. 972,670 filed Dec. 26, 1978.

BACKGROUND OF THE INVENTION

1. Field of the Invention

The invention relates to method and apparatus for characterizing a population of particles such as red blood cell typing for blood banking, while blood cell typing for histocompatibility or virus identification with specific antibodies, and other agents which bind with cells. The invention further relates to exploitation of specific cell receptors for analysis of the cells or samples reacting with the cells in an automatic analyzer.

2. Description of the Prior Art

In blood banking, the characteristics of red blood cells (blood typing) are usually determined by mixing a plurality of aliquots of the red cell suspension with different reagents and visually inspecting for agglomeration of cells. An automatic red cell typing system employing a flowing stream is manufactured by Technicon Corp. In this apparatus, the cell suspension is mixed with different reagents and the agglomerated cells are separated from disperse cells by decantation. Once again, the criterion of reaction is presence of agglomeration after mixing with a particular reagent.

In microbiology, organisms are generally characterized by their growth behavior in selected media. However, some identification is done by testing reaction with a panel of specific antibodies. The end point is often a form of precipitation. There are binding sites (receptors) on certain cells that are specific for certain ligands. These receptors are often the mechanism through which the ligand (often a hormone) performs its physiological functions. Cell receptor analysis often employs reaction of an aliquot of the cell population with radioactive ligand followed by separation of cell bound from free ligand. The radioactivity in one or both separated components is then measured. This is all done manually. The ligands are often vital hormones. Quantitation of both the ligand and the cell receptor are becoming important in clinical diagnosis. As the demand for such analysis increases, the manual procedure will give way to automation.

SUMMARY OF THE PRESENT INVENTION

One object of the present invention is to provide method and apparatus for the characterization of a population of cells or particles by means of novel suspending and sampling of test material and reagents into a flowing stream through specific ligand binder interaction using a novel means for separation of bound ligand from unbound ligand. An advantage of the separation means lies in its ability to retain gas bubbles in the liquid stream which reduce carryover at high throughput rates.

Another object of the present invention is to provide an automatic and continuous assay method for determination of ligand through specific ligand interaction with binding agent attached to cells or particles.

These and other objects of the present invention as will become apparent can be attained by the use of a method and apparatus wherein a precise amount of a solution of a known concentration of ligand, labeled, for example, with a radioactive isotope, and a liquid containing a suspension of cells or particles having specific binding sites affixed thereto is admixed with the sample solution containing either a known (standards for calibration) or unknown concentration of ligand to be measured which is reactable with the binding sites. The concentration of cells is so selected as to be insufficient to react with all the ligand present. This is true except in the case wherein the analyte is the cells. In that case a fixed concentration of labeled ligand in excess of the expected amount of binding agent is employed. The mixture is permitted to incubate for a fixed time interval. The incubated mixture is then separated into bound ligand fraction and unbound ligand fraction by separation means. One of these fractions is then directed to label measurement means where radioactivity is measured and recorded. A complication of radioactivity measurement is that a finite time (usually one minute) is required to perform a statistically reliable measurement. It is therefor desirable to perform a static rather than a dynamic measurement thereof. This has limited the throughput rate of previous automatic systems to less than one sample per minute. The liquid control means of the present invention overcomes this limitation.

In a continuous chemical analyzer, when a series of samples are sequentially introduced into a liquid stream, Skeggs and Technicon Corp. demonstrated that they may be spaced and separated from one another by the introduction of a wash or spacer liquid between each sample and multiple air bubbles segmenting the liquid stream without the likelihood of mixing such samples and with the aid of which samples of different characteristic may be analyzed continuously, one after another at brief intervals. One improvement of the present invention results from the introduction of a light absorbing material into either the sample mixture or the spacer liquid for control of operation. The presence of the light absorbing material is sensed by an in line optical detector. This in turn operates control means to perform required functions. A novel function of the control means resolves the throughput limitation of earlier automatic radioimmunoassay devices imposed by the static radioactivity measurement interval. In a simple inexpensive embodiment, the separated stream from the separation means is lead to a two way liquid deflector or valve. One way directs flow to waste, the other to a multiple container filling turntable such as one of the automatic fraction collectors in common use. When spacer liquid reaches the valve, the liquid is discarded until a sample mixture reaches the valve, which, under signal from optical detector, diverts the liquid stream into a fresh empty container. Alternate discarding of spacer and filling of tubes with sample provides a set of filled tubes ready for radioactivity measurement in any one of the many automatic test tube radioactivity measurement devices (gamma counters) in common use. Samples may be processed rapidly independent of radioactivity measurement. Radioactivity in the test tubes may be measured by a plurality of automatic gamma counters. If each one measures at the rate of one per minute, the overall rate would be equal to the number of counters per minute. Test tubes and their handling are eliminated in another embodiment of the invention having one or a plurality of self contained radioactivity measurement means. A channel or coiled channel contains the sample liquid mixture within the sensitive volume of each radioactivity measurement means. The optical detector actuated valve means is a multiport valve which directs the liquid flow into each of the coils in turn. On signal from optical detector means that spacer liquid has reached the valve, it directs the flow through a coil. The previous sample in the coil is flushed out with spacer liquid and the next sample fills the coil. The subsequent appearance of space liquid indicates the coil is filled with sample. Flow is now directed to the next coil and the static measurement interval begins for the sample trapped in the coil. Measurement interval continues for a time, usually one minute. If four coils and a four way valve are used, the system processes almost 4 samples per minute. Calibration means correct any nonuniformity of sensitivity. With self contained recording and data processing means, the system can provide direct output of quantitative results when standardized with known concentrations of analyte. When the system contains a single coil, a portion of the spacer liquid is used to flush the coil, and the balance is diverted to waste. The flow to waste begins when the coil is filled. This starts the counting interval. When the predetermined time interval is completed, the balance of the spacer liquid is directed to the coil where it flushes the old sample out before the sample fills it. Bubble retention throughout measurement reduces carryover between samples. When a continuous supply of cells is provided while a panel of different ligands are serially introduced, a color signal as described above is required. When the supply of cells is interrupted at each sampling, the optical properties of the cells (such as scatter) may provide the signal.

Means other than radioactivity may be used to label the ligand, such as coupling the ligand to an enzyme or making the ligand colored or fluorescent. The measuring means following separation of bound from unbound ligand would be an appropriate detector. A fluorescence label offers a simpler detection means than radioisotope labels, since measurement is more rapid and can be performed continuously as the separated stream flows past the detector. No valves or valve signalling is necessary.

Another object of the present invention is to provide novel method and apparatus for the separation of molecules bound to cells from molecules in solution in a continuously flowing stream and more particularly bound ligand from unbound ligand while retaining the bubble separation means of Skeggs. Ligands are generally small molecules of molecular weight several hundred. The cells or particles containing the binding agents are generally large in size. They often also have a smaller electrical charge to mass ratio. Consequently, after incubation of ligand and binding agent, we find two kinds of ligand, a small charged form and a very large form with lesser charge. This invention provides novel apparatus of simple and inexpensive construction to separate these two forms which comprises: a central channel through which flows the mixture of bound and unbound ligand; at least one additional parallel recipient flow channel adjacent the central channel and separated therefrom along its length by a semipermeable membrane of sufficient permeability to allow passage of the unbound ligand. Electrodes in at least two of the channels with electric potential applied thereto. The electric potential applies a driving force to the charged molecules or ions. The unbound ligand with a greater charge to mass ratio than the bound ligand, experiences a greater driving force across the membrane. Being of much smaller size it moves through the solution more rapidly. Being of much smaller size, it passes through the semipermeable membrane. The combination of all of these factors favors the movement of the unbound ligand over the bound ligand from the central channel to the recipient channel, resulting in the separation of the bound ligand in the central channel and the unbound ligand in the recipient channel. The extent of the separation will be influenced by the distance the unbound ligand must travel to reach the recipient stream. In a preferred embodiment a very thin, less than one millimeter, central channel is sandwiched between two parallel contiguous channels and separated therefrom by two semipermeable membranes. Each of the recipient channels contains an electrode. The electric field extends from the first recipient channel, across the first membrane, across the smallest dimension of the central channel, across the second membrane, to the electrode in the second recipient channel. All of the charged particles will tend to move out of the central channel in response to the electric field. A loss of ions may alter the composition of the incubated mixture unfavorably. For example, the ionic strength or acidity may change so much that ligand binding may be disrupted. By providing an ion containing stream on either side of the central channel, a charged particle from one recipient channel will tend to enter the central channel for every particle of like charge which leaves the central channel to the opposite recipient channel. This tends to stabilize the composition of the central channel. The flow rate through the recipient channels may be much greater than through the central to provide a surplus of ions and to wash away received ligand that has moved across by electric forces or by dialysis. In some cases dialysis may provide a considerable portion of the separation, it takes place independent of the electric forces. The length of said central channel is very great relative to the distance across said membranes so that the unbound ligand is exposed to the electric force for a prolonged period and the distance it must migrate for separation is very short.

The foregoing and other objects of the present invention will be described more fully in the following more detailed description of the invention.

BRIEF DESCRIPTION OF THE DRAWINGS

FIG. 1 is a schematic drawing of apparatus of the type to which the invention relates employing radioactivity labeled reagents, cell binding and electrical separation in an automatic analyzer.

FIG. 2 is a schematic drawing of apparatus of the type to which the invention relates employing fluorescent labeled reagents, cell binding and electrical separation in an automatic analyzer.

FIG. 3 is a schematic top view of a novel turntable for specimens containing cells.

FIG. 4 is a schematic side view of the turntable of FIG. 3.

FIG. 5 is a detail of the cell suspending portion of FIG. 4.

FIG. 6 is a section through line A—A of FIG. 5.

DESCRIPTION OF THE PREFERRED EMBODIMENT

Referring first to FIG. 1, peristaltic pump means 1 pulls fluids at precise rates through flexible tubing lines 2, metering the fluids. These lines terminate in air line 3, diluent pipet 4, buffer pipet 5, labeled ligand pipet 6, and sample pipet 7, shown immersed in their respective fluids in individual containers from which the contents are precisely metered. Cell binding analysis is carried out by addition of diluent 8 and radioisotope labeled ligand 9 to cell sample 10. Air bubbles from line 3 segment the stream, reducing carryover between samples. The combination of liquids is mixed and incubated to allow ligand to bind to cells in mixing coil 11 before passing into central channel 12 of separation means 13. Membranes 14 forming walls of central channel are of a pore size too small to permit passage of the cells, but large enough to permit passage of the much smaller unbound ligand molecules. A difference of electrical potential on electrodes 15 in recipient streams 16 provide an accelerating force on charged molecules in the central channel. Charged molecules, including unbound labeled ligand small enough to pass through the membrane are removed by this electrophoretic process and dialysis from the central channel into the recipient channels where they are swept away to waste 17 by the flow of buffer 18, preventing back diffusion. At the outlet of central channel 12 only cell bound radioactivity remains. Even if complete equilibrium between ligand and cell is not reached during incubation, the amount of radioactivity in the exit stream of central channel 12 will be a measure of the amount of binding ability of cell sample 10.

Sample container 10 is one of a plurality of samples on turntable 19.

After a fixed time interval, sample pipet 7 and labeled ligand pipet 6 lift out of their respective containers and into wash liquid containers. The turntable now advances one step to present another cell sample 10 to sample pipet 7 on the next cycle. The wash liquid reduces carryover between samples and indicates to optical sensor 20 that a cell free space is occuring between samples. Sensor 20 responds to the difference between a cell laden stream and a cell free stream by actuation of four position rotary valve 21 when cells disappear from the stream. To prevent false triggering by air segments, a time delay is built in, requiring continued absence of cells for a time longer than an air segment would cause. Liquid flows into central port of valve and out of one of the four exit ports to a coil 22 in one of the four radioactivity measuring devices 23. A suitable electrically operated valve is marketed by the Hamilton Company. The time delay of the signal from the optical detector is set long enough for the interface between reagent and wash liquid to enter the coil 22 before the valve 21 switches. The coil 22 in radioactivity measuring device 23 is large enough so that the entire cell reagent segment is contained therein. Upon switching, the entire segment containing the bound labeled ligand is trapped within the sensitive volume of the measuring device for a static measurement for a fixed time interval which is initiated by the same signal. While the next coil in sequence is being flushed and filled, the measuring continues. At the end of the measuring interval, the accumulated measurement is transmitted to the data processor and recorder module 24 and the device 23 is reset and ready for the next refill. After 3 more reagent segments have been inserted in turn in the other coils, the valve will again switch to this coil and spacer fluid will first wash out the old specimen to waste until a new cell specimen fills and is trapped in the coil. The air segments in the measuring coils do not interfere with measurement. In continuous analysis, Habig, R. L. Clin. Chem. 15,1045, 1969, demonstrated that retaining air segmentation throughout can reduce cross contamination to such an extent that throughput (samples/minute) can be considerably increased. If a new sample or standard is picked up every fifteen seconds, this system allows measuring intervals of at least 55 seconds while maintaining a throughput of 4 samples/minute. The nature of radioactive analysis requires a static measurement of almost a minute. This has limited the throughput of many present automatic radioassay systems. The present invention overcomes this limitation by freeing the processing of specimens from the measurement of radioactivity. Prior to the analysis of samples and standards, four identical specimens would ordinarily be entered into the system. These would eventually fill the 4 measuring devices 23 and the results of their measurement would be entered in processor 24. Any differences in values can be used to correct subsequent data for inequalities in sensitivity of the four detectors. Processor 24 may contain a modest computer for making such correction, formulation of standard relationships and calculation for concentrations of samples.

The foregoing describes the embodiment of the invention for quantitation of receptor on cell samples. When ligand on the cells is to be measured, labeled antibody is used as the reagent.

An embodiment of the invention for measuring the concentration of ligand in serum samples using cell receptors as binding agent would provide a plurality of serum samples in sample containers 10 on turntable 19. A continuous supply of a cell suspension is provided by cell pipet 25 in cell suspension 26 having cell suspending means to ensure a uniform supply. Since the cells will be continuously in the liquid stream, a color is provided in the wash liquid and optical sensor 20 responds to the loss of color when pipets 6 and 7 are lifted from the wash liquid.

FIG. 2 illustrates an embodiment of the present invention for measuring each of a plurality of cell samples against a panel of test reagents. An application would be in typing red blood cells in a blood bank. This system not only offers the advantages of automation, but quantitation replaces the all or none observation of cell clumping at the bottom of a test tube. In this embodiment, the reagent is labeled with a fluorescent indicator, but other labels such as radioisotope or enzyme may be employed with appropriate detection apparatus. Peristaltic proportioning pump means 1 pulls fluids at precise rates through flexible tubing lines 2 metering the fluids. These lines terminate in air line 3, labeled antibody pipet 27, cell sample pipet 7, buffer pipet 5, and diluent pipet 4 shown immersed in their respective containers. Cell binding analysis is carried out by aspirating cell suspension sample 10 on turntable 19 via pipet 7 and combining it with buffer 18 via pipet 5 and segmenting it with air bubbles from air line 3 to reduce carryover between samples. The combination of liquids is mixed in mixing means 11 then passed through central channel 12 of first electrical separation means 13. Membranes 14 are of a pore size too small to permit passage of the cells but large enough to permit passage of charged molecules which may interfere with the binding or the fluorescence of the final mixture. These are carried to waste 17 by buffer in recipient streams 16. By this initial separation, a more uniform test material with a reproducible milieu for the cells is provided. The cell stream emerging from the central channel 12 is mixed in second mixing means 30 with labeled antibody aspirated by pipet 27 from antibody container 28 on second turntable 29. Mixing means 30 is long enough to provide an incubation period for binding of antibody to cells before entering central channel 12 of second electrical separation means 31. Complete equilibrium is not required in this system. Membranes 14 are of a pore size too small to permit escape of cells but large enough to permit passage of charged antibodies not bound to cells. Antibody turntable 29 carries a plurality of different labeled antibodies in individual containers. Each one is reacted in turn with a single cell sample. The cell sample 10 is aspirated continuously while the antibody turntable 29 steps through the complete panel of different antibodies as antibody pipet 27 alternately dips in and out of antibody containers 28. The antibody pipet 27 may alternately dip into wash water between antibodies to reduce carryover. The cell stream emerges from central channel 12 of second separation means 31 where it is mixed in mixing means 32 with diluent from diluent pipet 4 to enhance or produce fluorescence. Buffer in recipient streams exiting second separation means 31 is also mixed with diluent liquid. These three streams pass through fluorescence detection means 33 then to waste 17. Fluorescence information is processed by data process means 34 to provide cell sample information.

Labeled reagents other than antibodies may be used. Agents which bind with cells and by their binding convey useful information may be used. The turntables are designed so that antibody turntable 29 makes a complete revolution before cell turntable 19 makes one step. Antibody turntable 29 may step through occupied positions at a slower pace and step through empty positions rapidly to prepare for the next cell sample. It is important that cells be uniformly suspended in the cell sample container during aspiration.

FIG. 3 shows a top view of a special turntable for cell suspension samples. FIG. 4 is a side view of a section through line B—B of FIG. 3. Sample support disc 35 on shaft 36 is rotated by stepping motor 37. Perforations 38 in disc 35 hold cup supports 39. These supports are molded of a lubricous plastic such as polyolefin. They snap into perforations and are held in place at an angle to the vertical by molded projections 40. An opening 41 in side of cup support 39 allows edge of flexible gear 42 to penetrate. Gear 42 is driven by slow speed motor 43. Sample cup 44 containing cell suspension rests in cup support 39 centered by inner pivot 45 in cup support. Sample cup has inner flutes 46 and outer flutes 47 molded therein. As shown in detail of FIG. 5 and FIG. 6 which is a section through line A—A of FIG. 5, the teeth of gear 42 penetrate the opening 41 in the support and engage the outer flutes of the sample cup causing it to rotate. Since the cup does not rest vertically, its rotation causes the inner flutes 46 to raise and lower portions of the contents, providing a gentle mixing suspending action. Gears are provided at the station having aspirating pipet 25 and at least one prior station.

While I have shown and described the preferred embodiments of my invention, it will be understood that the invention may be embodied otherwise than as herein specifically illustrated or described, and that certain changes in the form and arrangement of parts and in the specific manner of practicing the invention may be made without departing from the underlying area or principles of this invention within the scope of the appended claims.

What is claimed is:

1. Analysis apparatus for analyzing suspensions of cells, particles and the like or for analyzing solutions by the use of suspensions of cells, particles and the like, which comprises: means for flowing reaction mixtures, in turn, along a conduit, each of said reaction mixtures comprising a liquid phase and a particulate suspension phase including a suspension of particulate material such as cells, cell membranes, bacteria, viruses and the like, reaction taking place in said mixture to form a reaction product, at least, on said particulate material; electrical separation means along a portion of said conduit for separating reacted particulate material in each of said flowing reaction mixtures from certain other constituents of said reaction mixture by movement of said constituents across at least one permeable membrane means and into at least one other separate flowing recipient fluid stream under the force of electrical field means; and, downstream of said electrical separation means, means for determining a constituent of interest by analysis of said separated particulate suspension and/or said separated recipient fluid stream or streams.

2. Apparatus according to claim 1, which further includes: means for introducing an occluding inert fluid segment intermediate successive reaction mixtures to maintain said successive reaction mixtures discrete.

3. Apparatus according to claim 2, which further includes: means for introducing additional occluding inert fluid segments into said conduit to sub-divide each of said reaction mixtures.

4. Apparatus according to claim 2, which further includes: means for providing a wash liquid segment between successive reaction mixtures flowing in said conduit, each of said reaction mixtures being separated from adjacent wash liquid segments by at least an occluding inert fluid segment.

5. Apparatus according to claim 1, wherein said determining means includes means for measuring radioactivity, color, fluorescence or enzyme activity.

6. Apparatus according to claim 4, which further includes: means intermediate said electrical separation means and said determining means for detecting the passage of each of said separated reaction mixtures and/or separated constituent flowing along its respective channel, and means responsive to said detecting means for actuating fluid flow directing means for directing firstly that portion of the separated flowing stream containing the constituent of interest to isolation channel means within said determining means and for directing secondly at least a portion of the wash segment of said stream intermediate successive segments containing constituent of interest to waste, while the constituent of interest is being determined within said isolation channel means.

7. Apparatus according to claim 6, which further includes: said determining means comprising a plurality of individual flow through radioactivity measuring means; said fluid flow directing means comprising multiple position valve means for conducting said separated flowing stream to one of a plurality of isolation channel means within the sensitive volume of radioactivity measurement means, whereby appearance of the wash segment of said flowing stream intermediate successive segments containing constituent of interest causes said fluid flow directing means to isolate one segment containing constituent of interest in one of said fluid isolation channel means for radioactivity measurement while a next wash segment is directed to flush out a next isolation channel means prior to a next segment containing constituent of interest entering said next channel for isolation and measurement.

8. Apparatus according to claim 6, which further includes: said fluid flow directing means comprising a fluid conduit for conducting said portions, positionable between a first position wherein fluid is conducted to one of a series of fluid portion containers wherein the isolated individual portion of the separated flowing stream containing the constituent of interest will be stored for later determination, and a second position wherein fluid stream is conducted to waste to discard said wash segment portion; container moving means to move previously filled container out of alignment with, and an empty container into alignment with said first position of said positionable conduit for filling with next individual portion of stream containing the constituent of interest after wash segment portion is discarded.

9. Apparatus according to claim 1, which further comprises: dispensing means for dispensing seriatim a plurality of different suspensions for analysis; dispensing means for dispensing seriatim a plurality of different solutions for analysis; and dispensing control means for controlling dispensing each of said different suspensions in combination with and for admixture with each of said different solutions or in other selected combinations.

10. Apparatus according to claim 1, which further comprises: dispensing means for dispensing seriatim a plurality of different suspensions for analysis; a plurality of suspension containers for containing said suspensions; and suspending means for maintaining homogeneity of said suspensions in said suspension containers.

11. Apparatus according to claim 10, which further comprises: suspension container support means for supporting said suspension containers in a non vertical rotatable condition; internal projection means within said containers which serve to agitate its contents upon rotation of said containers; and container rotation means for rotating said containers.

12. Apparatus according to claim 11, which further comprises: suspension containers having external projection means thereon for engagement with rotating means to impart rotation to said containers to provide mixing means to maintain homogeneity of the contained suspension.

13. The apparatus according to claim 10, which includes suspension containers having internal fluting means and external fluting means, said external fluting means for engagement with rotating means for rotation of said containers, and said internal fluting means for providing gentle agitation of the contained suspension upon rotation of said containers.

14. Apparatus according to claim 1, which further comprises: at least one additional electrical separation means along a portion of said conduit for altering the composition of the fluid passing therethrough by removing certain constituents to enhance the analytical process; and reagent addition means intermediate said different electrical separation means for addition of reagent to the fluid leaving an electrical separation means to alter the composition of said fluid prior to its entry into another electrical separation means to enhance the analytical process.

15. Apparatus according to claim 1, which further comprises reagent addition means along said separated fluid stream intermediate said electrical separation means and said determining means for altering the composition of the fluid to facilitate the determination of the constituent of interest in said determining means.

16. Apparatus according to claim 1, wherein said electrical separation means further comprises: a central channel means for said flowing reaction mixture; at least one additional parallel flow channel means adjacent said central channel means for said separate recipient fluid stream and separated therefrom along its length by said permeable membrane means, said membrane means being sufficiently permeable to allow passage of at least one of said constituents; electrode means in at least two of said channel means; means for applying a difference of electrical potential across said electrode means for providing said electrical field means for said movement of said constituent across said membrane means and into said flowing recipient stream in said adjacent parallel flow channel means.

17. Apparatus according to claim 1, wherein said electrical separation means further comprises; first and second member means, each having a surface with groove means therein, said groove means having fluid inlet and outlet means; electrode means in said groove means; an inner member means having slot means, said slot means having inlet and outlet means; mounting means for said first and said inner member means in confronting face to face relation with said groove means in registry with said slot means, and for mounting said second and said inner member means in confronting face to face relation with said groove means in registry with said slot means at another face of said inner member means; permeable membrane means interposed between said first and said inner member means and permeable membrane means interposed between said second and said inner member means, so as to form three fluid channels with common permeable walls between said channels, said flowing reaction mixture flowing through one of said channels via said inlet and outlet means; said other separate flowing recipient fluid streams flowing through the other said channels via said inlet and outlet means; and electrical means for applying a difference of electrical potential across said electrode means to provide said electrical field means.

18. Apparatus according to claim 17, which further comprises: a plurality of inner member means with slot means mounted in registry; a plurality of permeable membrane means interposed between individual inner member means and between outermost of said inner member means and said first and second member means so as to form a plurality of fluid channels with common walls therebetween.

19. Apparatus according to claim 17, wherein said groove means is formed by a combination of a separate slotted member means applied to a flat member means.

20. Apparatus according to claim 16, wherein the distance between channels is short relative to the length of said channels, providing a short exit path for migrating constituents and a relatively long exposure to the electrical driving force.

21. Apparatus according to claim 1, wherein said electrical separation means further comprises: first and second member means, each having a surface with groove means therein, said groove means having fluid inlet and outlet means, electrode means in said groove means; means for mounting said first and second member means in confronting face to face relation with said groove means in registry; permeable membrane means interposed between said first and said second member means so as to form two fluid channels with a common permeable wall therebetween.

22. A method of analyzing suspensions of cells, particles and the like or for analyzing solutions by the use of suspensions of cells, particles and the like, which comprises the steps of:

(a) forming a plurality of flowing reaction mixtures, each of said mixtures comprising a liquid phase and a particulate suspension phase including a suspension of particulate material such as cells, cell membranes, bacteria, viruses, and the like, reaction taking place in said mixture to form a reaction product, at least, on said particulate material;
(b) flowing each said reaction mixture in turn continuously along a conduit;
(c) flowing each said reaction mixture in turn through electrical separation means to separate reacted particulate material from certain other constituents of said reaction mixture by movement of said constituents across at least one permeable membrane means and into at least one other separate flowing recipient stream under the force of electrical field means;
(d) and determining at least one constituent of interest by analysis of the separated particulate suspension and/or the separated recipient fluid stream by determining means downstream of said electrical separation means.

23. A method according to claim 22, further comprising the steps of: flowing fluid to be analyzed through a first electrical separation means for altering the composition of said fluid by the removal of certain constituents to enhance the analytical process and; addition of reagent to the fluid leaving said first electrical separation means to alter the composition of said fluid prior to its entry into a second electrical separation means to facilitate analysis.

24. A method according to claim 22, further comprising the step of adding reagent to said separated fluid stream intermediate said electrical separation means and said determining means for altering the composition of the fluid to facilitate the determination of the constituent of interest.

* * * * *